US00PP37138P2

(12) United States Plant Patent
Cho

(10) Patent No.: US PP37,138 P2
(45) Date of Patent: Dec. 9, 2025

(54) ***COLOCASIA* PLANT NAMED 'Hawaiian Luau'**

(50) Latin Name: *Colocasia esculenla*
Varietal Denomination: Hawaiian Luau

(71) Applicant: John Cho, Kula, HI (US)

(72) Inventor: John Cho, Kula, HI (US)

( * ) Notice: Subject to any disclaimer, the term of this patent is extended or adjusted under 35 U.S.C. 154(b) by 0 days.

(21) Appl. No.: 19/045,644

(22) Filed: Feb. 5, 2025

(51) Int. Cl.
*A01H 6/10* (2018.01)
*A01H 5/12* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/12
See application file for complete search history.

*Primary Examiner* — Keith O. Robinson
(74) *Attorney, Agent, or Firm* — Weatherly IP Solutions, LLC; James M. Weatherly

(57) ABSTRACT

A new cultivar of *Colocasia* plant named 'Hawaiian Luau' that is characterized by vigorous but compact plant habit with multiple basal branches giving rise to a high leaf count and a rapidly produced full plant for growing in containers or in the landscape. The leaves of 'Hawaiian Luau' are dark grey-blue in color with a matte surface texture. The leaf veins and midrib of 'Hawaiian Luau' are light yellow-green in color, is disclosed.

2 Drawing Sheets

Genus and species: *Colocasia esculenta.*
Variety denomination: 'Hawaiian Luau'.

BACKGROUND OF THE NEW PLANT

The present invention relates to a new and distinct variety of *Colocasia* commonly known as the taro plant or elephant ears. *Colocasia* is grown as a food crop and for use as an ornamental plant in containers or in the landscape. The new cultivar is known botanically as *Colocasia esculenta* and will be referred to hereinafter by the cultivar name 'Hawaiian Luau'.

*Colocasia* is a tuberous rooted perennial which is native to tropical Asia and Polynesia. Native plants of *Colocasia* grow to 1.5 m to 2 m in height from starchy tubers. The leaves of *Colocasia* are heart-shaped and typically are very large in size.

The new *Colocasia* variety named 'Hawaiian Luau' is the product of a formal breeding program carried out by the inventor in a cultivated area in Wailuku, Hawaii. The purpose of the breeding program is to develop new commercial varieties by combining attributes not found in currently commercially available varieties.

'Hawaiian Luau' is a seedling selection from the controlled pollination, namely the inventor's variety of *Colocasia* plant named 'Maui Gold' (U.S. Plant Pat. No. 24,482) as the male parent, and a breeding line known to the inventor as '2001-28' (unnamed, unreleased, unpatented) as the female parent. The inventor selected 'Hawaiian Luau' in 2018.

'Hawaiian Luau' exhibits a vigorous but compact plant habit with multiple basal branches giving rise to a high leaf count and a rapidly produced full plant for growing in containers or in the landscape. The leaves of 'Hawaiian Luau' are dark grey-blue in color with a matte surface texture. The leaf veins and midrib of 'Hawaiian Luau' are light yellow-green in color.

The most commonly employed means of asexual propagation of the genus *Colocasia* is the excision and replanting of a shoot which consists of the apical 1 cm to 2 cm portion of the plant corm with the attached basal 15 cm to 20 cm portion of the petiole. In regions of the world where *Colocasia* is grown, this plant shoot is known as a "huli", and the means of propagation is known as "huli propagation", whereby the apical shoots are separated from the plant by cutting the shoot at the top of the corm immediately above the newest leaf scar and planted. The inventor first propagated 'Hawaiian Luau' by the method of huli propagation in 2018. Evaluation in field and pot studies have confirmed that the unique features of 'Hawaiian Luau' are stable and uniform, and that 'Hawaiian Luau' reproduces true to type in successive generations of asexual propagation by huli propagation and by tissue culture.

SUMMARY

The following traits have been repeatedly observed and represent the distinguishing characteristics of the new *Colocasia* cultivar 'Hawaiian Luau'. These traits in combination set 'Hawaiian Luau' apart from all other existing varieties of *Colocasia* known to the inventor. 'Hawaiian Luau' has not been tested under all possible conditions and phenotypic differences may be observed with variations in environmental, climatic and cultural conditions, however, without any variance in genotype.

1. 'Hawaiian Luau' grows vigorously while remaining compact with prolific basal branching and high leaf count.
2. The first three or four leaves after planting a tissue-cultured young plant of 'Hawaiian Luau' are entirely mid-green in color. Subsequent leaves on a mature plant of 'Hawaiian Luau' are dark grey-blue in color and bear light yellow-green veins and midrib.
3. The leaves of 'Hawaiian Luau' are presented slightly folded along the midrib.

4. The petioles of the leaves of 'Hawaiian Luau' emerge green in color and become burgundy in color at leaf maturity and darker burgundy towards the piko attachment at the leaf underside.
5. The upper and lower surfaces of the leaves of 'Hawaiian Luau' are matte.
6. The midrib veins and primary lateral veins of the leaves of 'Hawaiian Luau' are cream-yellow in color and are prominently raised on the leaf undersides (abaxial surfaces).

BRIEF DESCRIPTION OF THE PHOTOGRAPHS

The accompanying color photographs illustrate the overall appearance of 'Hawaiian Luau' showing the colors as true as it is reasonably possible to obtain in colored reproductions of this type. Colors in the drawing may differ from the color values cited in the detailed botanical description, which accurately describe the actual colors of the new variety 'Hawaiian Luau'.

Figure 1:
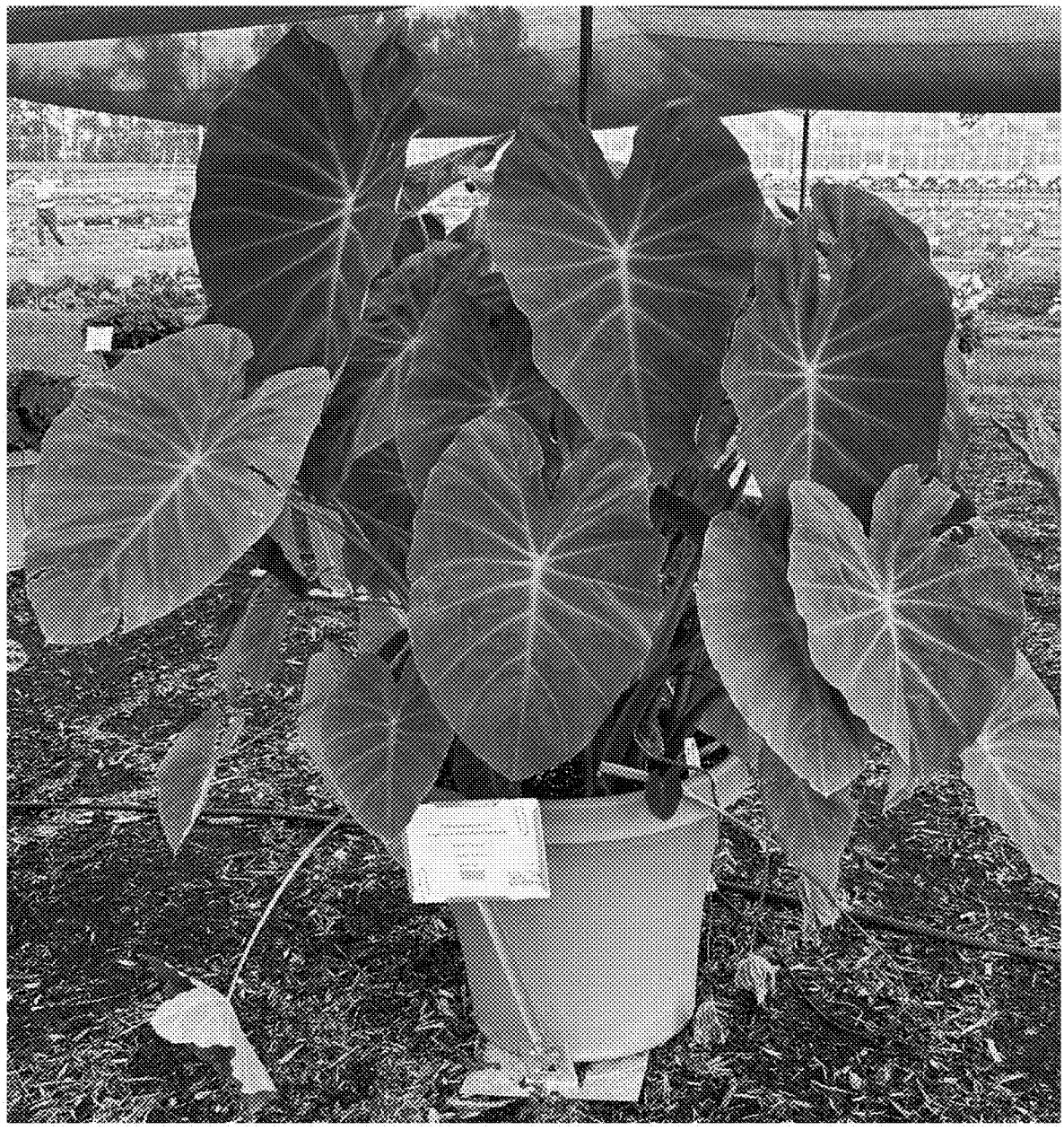
FIG. 1 shows a mature plant of 'Hawaiian Luau'.
Figure 2:
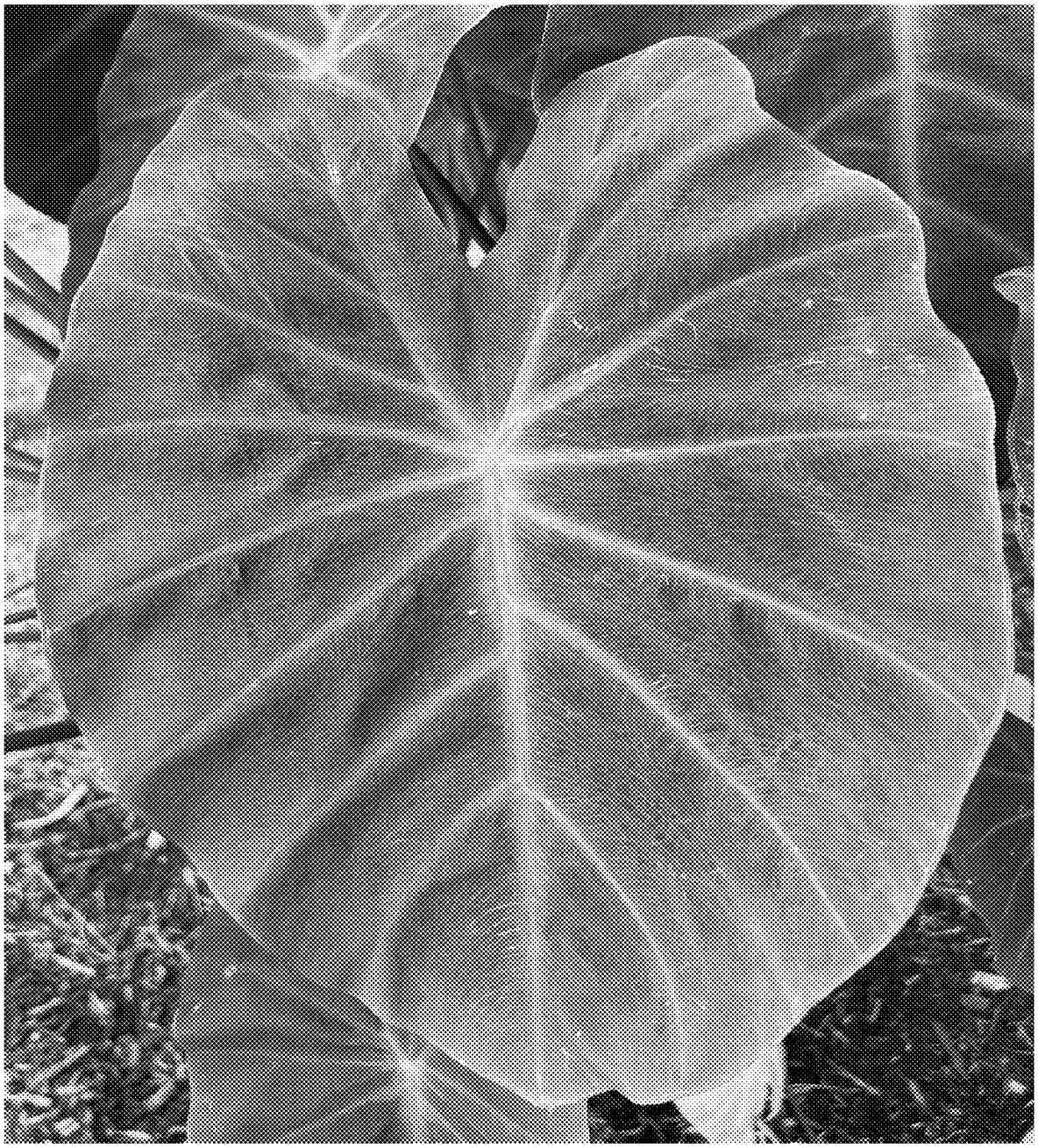
FIG. 2 shows a close-up of a leaf of 'Hawaiian Luau'.

The photographs were made from a plant which is approximately 24 months old from a tissue culture division and which had been grown outdoors in Santa Barbara, California. No growth regulators had been applied.

BOTANICAL DESCRIPTION OF THE PLANT

The following is a detailed description of the new *Colocasia* plant named 'Hawaiian Luau'. Data was collected from a mature plant which was 24 months old and grown outside in a 3-gallon container in Santa Barbara, California. The color determinations are in accordance with the 2007 edition of The Royal Horticultural Society Colour Chart, London, England, except where general color terms of ordinary dictionary significance are used. The growing requirements are similar to other *Colocasia*.

Botanical classification:

*Genus.*—*Colocasia.*

*Species.*—*Esculenta.*

*Variety.*—'Hawaiian Luau'.

*Common name.*—Taro or elephant ears.

Parentage:

*Male parent.*—*Colocasia* plant named 'Maui Gold' (U.S. Plant Pat. No. 24,482).

*Female parent.*—Proprietary breeding line 2001-28 (unreleased, unnamed, unpatented).

Plant description:

*Use.*—Container or landscape plant.

*Cultural requirements.*—In common with all *Colocasia*, 'Hawaiian Luau' thrives in high temperatures (above 70° F.), in full sun or partial shade, and is most vigorous when well-watered.

*Root system.*—Tuberous.

*Roots.*—Fleshy, up to 4 mm in diameter, with fibrous and fine lateral roots; color 155B.

*Root development.*—At soil temperatures 20° C. to 25° C., root initials are evident within 3 days. Roots will reach the edge of a 1 gallon container in 14 days.

*Plant vigor.*—Vigorous basal branching, forming dense canopy of leaves and stems.

*Plant growth habit.*—Upright, domed, non-spreading.

*Plant growth rate* (*crop time*).—A one-gallon container plant may be produced in 12 to 16 weeks from a 4 cm cell transplant. A large specimen plant of 'Hawaiian Luau' may be grown in a 3-gallon container in 24 months from a 4 cm cell transplant.

*Plant description.*—Once a huli or corm is introduced into the soil and the plant is established, additional corms or cormels are produced, attached to the original corm. These cormels give rise to new lateral shoots. A one year old plant of 'Hawaiian Luau' produces 25 to 35 lateral shoots. Lateral shoots begin to appear above soil level about 6 to 8 weeks after planting of the initial plant.

*Corm* (*formed at base of each petiole or huli*).—Shape and dimensions: Short cylindrical, 2 cm to 3 cm in diameter, 1 cm in height. Surface texture: Rough with root initials (eyes). Color ranges between N186A and 202A.

*Cormels* (*arising from established primary corm, forming base of new lateral shoot*).—Arrangement: Cormels detachable from primary corm, clustered and forming base of new lateral shoot. Shape and dimensions: Short cylindrical, 1.0 cm to 2.5 cm in diameter, 0.5 cm in height. Surface texture: Rough with root initials (eyes). Color ranges between N186A and 202A.

*Plant dimensions.*—75 cm to 90 cm in height and 60 cm to 75 cm in width.

*Plant hardiness.*—USDA Zone 7b.

*Propagation.*—Propagation is accomplished by huli propagation and by tissue culture.

*Time to develop daughter plants.*—Appear above soil around 2 to 3 months after planting.

*Crop time.*—1.5 to 2.5 months.

Foliage (lateral shoots):

*Petioles.*—Shape: Round section. Petiole tapers towards leaf attachment. Length: 30 cm to 45 cm. Diameter: 10 mm as petiole emerges from sinus, tapering to 5 mm just below piko attachment to abaxial leaf surface. Strength: Strong, arches under the weight of the leaf. Color: Emerges 146C becoming uniformly 61A with 59B towards piko attachment to abaxial leaf surface. Surface texture: Glabrous, semi-glossy. Sap color: Colorless.

*Leaf.*—Number: Each lateral shoot bears 1 to 5 leaves at a time. Observed plant has 35 to 45 leaves of all ages. Dimensions at maturity: 40 cm in length and 25 cm in width. Average leaf sinus depth (mature leaf): 7 cm. Attitude: Oblique. Aspect: Erect with apex down. Leaf folded along vein midrib until flat when fully mature. Shape: Sagittate. Margins: Entire, slightly undulating. Margin color: Adaxial surface: Marginal band 3 mm in width. Margin band colors 198C and 198D. Abaxial surface: Marginal band 3 mm in width, present between abaxial veins only. Margin band color: N189B. Apex: Narrowly rounded. Base: Peltate. Surface: Semi-glossy. Attachment: Petiolate with characteristic tissue formed at junction of leaf blade with the upper termination of the petiole. This area of the leaf tissue is also known as the "piko" and is evident by virtue of its upper surface color being similar to the color of the petiole. The principal veins radiate from the piko. Piko color: 185A. Leaf sheath: Open. Leaf surface: Adaxial surface: glossy; abaxial surface: matte. Leaf color (both surfaces except central white to cream-yellow streak): Ranges between N187A and 202A, but not as black as 202A. Length: 40 cm.

Width (leaf base): 7 cm to 9 cm. Venation: Palmate. Veins (adaxial leaf surfaces): Description: Broad midrib and primary lateral veins, multiple narrow subsidiary veins extending through the laminae between the midrib and lateral veins. Quantity: In total, 6 primary lateral veins on each side of the midrib, of which 3 radiate from the piko and 3 extend from the midrib between the piko and leaf apex. Midrib dimensions, profile: Tapering in width from 8 mm towards piko, reducing to 2 mm in width towards leaf apex. Not raised or depressed. Midrib color: 191C. Primary lateral veins dimensions (both leaf surfaces): Tapering in width from 4 mm towards piko, reducing to 1.5 mm to 2 mm towards leaf margin. Primary lateral veins color (both leaf surfaces): 191C Primary lateral veins profile (adaxial leaf surfaces): Flat. Primary lateral veins dimensions (abaxial leaf surfaces): Prominently raised, hemispherical section, height above leaf abaxial surface: 3 mm to 4 mm. Subsidiary small veins (adaxial and abaxial leaf surfaces): Description: Numerous within leaf lamina, narrow, fine and either running at right angles to lateral vein or internally parallel with lateral veins. Color (adaxial surface): Ranging between grey-white 156D and grey 202B. Color (abaxial surface): Color not found in Colour Chart but darker than 202B and less dark than 202A.

Inflorescence, flowers, reproductive organs and seed:

*Inflorescence*.—The inflorescence arises from the leaf axils. The inflorescence is made up of a short peduncle, a spadix, and spathe.

*Spadix*.—The spadix is botanically a spike, with a fleshy central axis to which the small sessile flowers are attached. The spadix is 9.5 cm to 10 cm long, with female flowers at the base, male flowers towards the tip, and sterile flowers in between, in the region compressed by the neck of the spathe. The extreme tip or appendage of the spadix has no flowers at all. The top and bottom portions of the spadix are separated by a narrow neck region, corresponding to the region of the sterile flowers on the spadix.

*Spathe*.—The spathe is a large yellowish bract, 19.5 cm to 21.5 cm long, which sheathes the spadix. The lower part of the spathe is light-green (150B) in color and wraps tightly around the spadix and completely occludes the female flowers from view. The top portion of the spathe is yellow (13C) in color and is rolled inward at the apex, but is open on one side to reveal the male flowers on the spadix.

*Seed*.—Seed is not produced naturally since male and female flowers within each inflorescence do not mature at the same time.

Diseases and pests: In common with *Colocasias* in general, 'Hawaiian Luau' is susceptible to attack by *Tetranychus urticae*, commonly known as red spider mite. Otherwise, the inventor has not observed that 'Hawaiian Luau' is more or less susceptible to pests or diseases than other cultivars of the genus.

COMPARISON WITH PARENTAL LINES

'Hawaiian Luau' is distinguishable from its parent by leaf color (male parent) and by the color of the leaf petioles (female parent). Whereas the leaves of 'Hawaiian Luau' are dark grey-blue in color with a matte surface texture, the leaves of 'Maui Gold' are chartreuse-green in color a glossy surface texture. Whereas the petioles of 'Hawaiian Luau' are light purple in color, the petioles of '2001-28' are darker red-purple (burgundy) in color.

COMPARISON WITH KNOWN VARIETY

The closest comparison variety in commerce known to the inventor is the inventor's variety of *Colocasia* plant named 'Tropical Storm' (U.S. Plant Pat. No. 28,567). Whereas the background leaf colors of 'Hawaiian Luau' and 'Tropical Storm' are similarly dark grey-purple in color and matte in surface texture, the leaves of 'Tropical Storm' exhibit prominent broad cream-yellow midribs which color spreads into the adjacent leaf laminae. In contrast, the leaves of 'Hawaiian Luau' exhibit narrow cream-yellow narrowly defined midribs. The leaves of both varieties 'Tropical Sunrise' and 'Hawaiian Luau' are matte in surface texture and are borne on similar burgundy-red petioles.

I claim:

1. A new and distinct cultivar of *Colocasia* Plant Named 'Hawaiian Luau' as illustrated and described herein.

* * * * *